(12) United States Patent
Mundrigi et al.

(10) Patent No.: US 10,384,168 B2
(45) Date of Patent: Aug. 20, 2019

(54) MEMBRANE WITH PERFORMANCE ENHANCING MULTI-LEVEL MACROSCOPIC CAVITIES

(71) Applicant: Sartorius Stedim Biotech GmbH, Göttingen (DE)

(72) Inventors: Ashok Mundrigi, Bangalore (IN);
Jahnavi Gowda, Bangalore (IN);
Ramesh Mundlamuri, Bangalore (IN);
Thomas Loewe, Göttingen (DE);
Holger Linne, Göttingen (DE);
Sebastian Handt, Göttingen (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 51 days.

(21) Appl. No.: 15/325,766

(22) PCT Filed: Jul. 15, 2015

(86) PCT No.: PCT/EP2015/001453
§ 371 (c)(1),
(2) Date: Jan. 12, 2017

(87) PCT Pub. No.: WO2016/008586
PCT Pub. Date: Jan. 21, 2016

(65) Prior Publication Data
US 2017/0165611 A1   Jun. 15, 2017

(30) Foreign Application Priority Data

Jul. 18, 2014   (IN) .......................... 3544/CHE/2014

(51) Int. Cl.
*B01D 67/00* (2006.01)
*B01D 69/06* (2006.01)

*A23L 2/74* (2006.01)
*B01D 61/14* (2006.01)
*B01D 71/68* (2006.01)
(Continued)

(52) U.S. Cl.
CPC .............. *B01D 67/009* (2013.01); *A23L 2/74* (2013.01); *B01D 61/14* (2013.01); *B01D 67/0086* (2013.01); *B01D 69/06* (2013.01); *B01D 71/68* (2013.01); *C02F 1/444* (2013.01); *C12H 1/063* (2013.01); *C12N 1/02* (2013.01); *A23V 2002/00* (2013.01); *B01D 2325/06* (2013.01); *B01D 2325/08* (2013.01); *C02F 2303/04* (2013.01)

(58) Field of Classification Search
None
See application file for complete search history.

(56) References Cited

U.S. PATENT DOCUMENTS

| 3,724,673 | A | 4/1973 | Ryon |
| 4,964,992 | A | 10/1990 | Goldsmith et al. |

(Continued)

FOREIGN PATENT DOCUMENTS

| CA | 2397022 | 2/2003 |
| DE | 102011117900 | 5/2013 |

(Continued)

*Primary Examiner* — Chinessa T. Golden
(74) *Attorney, Agent, or Firm* — McDonnell Boehnen Hulbert & Berghoff LLP

(57) ABSTRACT

The present invention relates to a micro-porous filtration membrane with performance enhancing multi-level macroscopic cavities as well as a method for producing the same.

9 Claims, 8 Drawing Sheets

(51) Int. Cl.
  *C02F 1/44* (2006.01)
  *C12H 1/07* (2006.01)
  *C12N 1/02* (2006.01)

(56) References Cited

U.S. PATENT DOCUMENTS

| | | |
|---|---|---|
| 5,458,951 A | 10/1995 | Kagawa |
| 6,132,845 A | 10/2000 | Heinzlreiter |
| 6,203,741 B1 | 3/2001 | Heinzlreiter |
| 7,309,385 B2 | 12/2007 | Hong et al. |
| 8,728,214 B2 | 5/2014 | Maurer |
| 2003/0121841 A1 | 7/2003 | Harttig et al. |
| 2005/0082215 A1 | 4/2005 | Swenson |
| 2006/0016685 A1 | 1/2006 | Hawkins et al. |
| 2006/0121267 A1* | 6/2006 | Tsuyumoto ........ B01D 67/0009 428/315.7 |
| 2012/0273421 A1* | 11/2012 | Perry ................ B01D 61/027 210/651 |

FOREIGN PATENT DOCUMENTS

| | | | |
|---|---|---|---|
| EP | 2 366 449 | 9/2011 | |
| WO | WO 1993/11861 | 6/1993 | |
| WO | WO 2000/38823 | 7/2000 | |
| WO | WO 2012/153050 | 11/2012 | |
| WO | WO 2014/039894 | 3/2014 | |
| WO | WO-2014039894 A1 * | 3/2014 | ........... B01D 61/025 |

\* cited by examiner (a)

(b)

MEMBRANE WITH PERFORMANCE ENHANCING MULTI-LEVEL MACROSCOPIC CAVITIES

FIELD OF THE INVENTION

The present invention relates to a micro-porous filtration membrane with performance enhancing multi-level macroscopic cavities as well as a method for producing the same.

BACKGROUND OF THE INVENTION

Generally, the service life of membrane filters is directly dependent on their dirt holding capacity. This is also known as total throughput, the maximum volume quantity Vmax of a liquid solution filtered before the filter is blocked by any particulate contained in the solution. The blocking effect is often based on particulate deposition on the non-filtrate surface of the filter material. Filtration is understood to mean a method for separating solid particles or molecules from a fluid (i.e. liquids or gases), even insoluble liquid droplets from another liquid (emulsion) or from gases (aerosols). A common, essential feature of filtration is that a porous medium, such as a filter paper or membrane, is perfused by the continuous phase (i.e. a liquid or gas), with the solid particles, molecules, or droplets being retained (retention) at the same time on the surface of the porous medium or inside.

Porous membranes are used mainly in the methods of ultrafiltration, of microfiltration, and of dialysis. Whether a particle or molecule is retained by ultrafiltration membranes or microfiltration membranes depends, in addition to the operating conditions, in particular on its size and structure relative to the size and structure of the membrane pores. A typical area of use of microfiltration is, for example, the concentration of suspensions, whereas ultrafiltration is often used for fractionating dissolved low-molecular-weight materials and macromolecules. A complete separation with ultrafiltration requires in this context that the molecular weights of the materials to be fractionated differ by at least one order of magnitude.

The pore size of microfiltration (micro-porous) membranes is in the micrometer range, typically from about 0.08 to about 10 µm. The pore size of ultrafiltration membranes is mostly defined by specifying the limit at which 90% (or 95%) of the molecules of a particular molar mass are retained (molecular weight cutoff, MWCO).

The above-mentioned surface blocking behavior, which may be also referred to as clogging, is specifically present in the field of micro-porous membranes which are commonly applied to sterilizing processes in food and beverage filtration of water, wine, beer or biopharmaceutical filtration of cell and bacteria nutrition media or clarification and purification filtration of cell and bacteria broths. In the aforementioned processes, the particulates present in the feed to be filtered show typically a broad distribution, commonly in terms of a Gaussian distribution. Many of the filter devices used in these applications contain two different layers of membrane material. The first layer to be passed by the non-filtrate (feed) is designed for high total throughput, i.e. to retain particulate without being blocked by those as far as possible. The second layer, which is most often a layer with a smaller pore size, is designed to have a sterilizing effect to fully retain small contaminants to be removed from the filtrate, such as microorganisms like bacteria. The enhancement of total throughput and flow rate is primarily targeted to the first layer, less to the sterilizing layer in order to keep this free of defects for the retention of e.g. microorganisms.

The easiest way to increase the total throughput is to enlarge the filter area as such, i.e. the three-dimensional size of the filter material. The enlargement of the filter area is accompanied with higher costs due to an increased amount of the filter material and larger filter device sizes. As a compromise, the filter device size can be kept constant by maintaining its outer dimensions. In such a case, the higher quantity of filter material has to be arranged more compacted in the same device size. The higher compaction results in higher hydrodynamic resistance or vice versa lower flow rates at given pressure difference between the non-filtrate side and the filtrate side of the filter.

In order to increase the flow performance and total throughput of filter materials, several attempts have been proposed in the last decades. For example, DE 10 2011 117 900 A1 discloses a pleated filter element to be used for the filtration of e.g. oil-based suspensions, dispersions or emulsions, comprising a pre-filter layer and a main filter layer. The pre-filter layer comprises recesses which at least partially penetrate into the filter or completely penetrate through the filter layer. The recesses, which may be arranged in form of a pattern, increase the effective filter area and thus the dirt holding capacity of the filter element.

U.S. Pat. No. 6,203,741 B1 and U.S. Pat. No. 6,132,845 A describe methods for forming micro spike thermoplastic liners to be used for sealing tunnels, excavation sites, landfills, i.e. being liquid-impermeable, having at least one roughened surface with a plurality of irregularly shaped projections extending therefrom, which are preferably arranged in a regular pattern, at equal intervals to define columns and rows. The combination of the projections and the roughened surface allows the liner to frictionally engage a desired location. The liners are formed by a calendering process in which a smooth thermoplastic sheet is fed into a calender, which causes the smooth sheet to be formed as a thermoplastic liner having projections extending from one surface thereof.

CA 2 397 022 A1 describes a flat permeable membrane which may consist of polyether sulfones, having recesses on at least one side, wherein the dimensions of the recesses exceed the nominal pore size of the membrane by at least five-fold. The recesses, which may be in form of channels, have an average diameter of 5 to 500 µm, whereas the nominal pore size of the membrane is in the range from 0.2 nm to 5 µm. The thickness of the membrane is described to be from 1 µm to 1000 µm. Said membranes are produced by preparing a substrate, such as a silicon wafer, which has protrusions on its surface as a negative for the desired recesses, applying the membrane material or a precursor thereof onto the substrate and forming the porous membrane on the substrate using solvent evaporation and/or replacing the solvent with a precipitating agent.

U.S. Pat. No. 2006/0016685 A1 discloses textured ion exchange membranes for use in an electrochemical cell, said membranes comprising an anion exchange layer abutting a cation exchange layer to form a heterogeneous water-splitting interface there-between, and a textured surface having a pattern of texture features comprising spaced apart peaks and valleys, wherein the peak to peak distance (dpp) is at least 10 µm and the peak to valley distance (dpv) is at least 10 µm, whereas the aspect ratio dpv/dpp is 0.1 or more.

EP 2 366 449 A2 discloses a polymer membrane having repetitive convex-concave patterns formed on a surface in contact with a fluid to be treated. The membrane which may be made of a polysulfone-based material, has improved permeability and fouling properties, particularly when having a surface roughness of 1.1 to 1.5. The pattern of the membrane may be made using soft lithography technique used to form patterns in the technical field of semiconductors.

U.S. Pat. No. 7,309,385 B2 discloses a gas separation membrane of two or more layers comprising a supporting layer and an organic, porous, gas-permeable separating layer which may be made of polysulfone. The separating layer has a high effective separation area formed in terms of a three-dimensional nanostructure, which may be in form of protruded portions in tube form having a length of several tens nanometers to several millimeters, whereas the thickness of the protruded portion is several nanometers to hundred nanometers.

Further, in U.S. Pat. No. 3,724,673, a thin textured gas-permeable membrane for use in blood oxygenators and dialyzers is described, which comprises a film comprised of thermoplastic material having a myriad of thermoplastically formed deformations or undulations in terms of cones. These cones are plastically deformed in the membrane surface by localized bending and stretching in which case the cone regions are actually thinner than the parent membrane on which they are formed. The deformations or fine undulations constituting the texture are formed by placing a smooth membrane over a die on which a field of cones stands out in relief and applying a vacuum between the die and membrane, so that air pressure deforms the latter in correspondence with the cone pattern.

Further, DE 10 2008 045 621 A1 discloses a gas-permeable and liquid-impermeable membrane used, for instance, for gassing or for gas exchange in blood, wherein the membrane is structured on at least one side, particularly on the non-filtrate side, which may consist of polyether sulfones. The membrane comprises channels and/or branched pathways which may either be in form of through-passages throughout the entire membrane or partially penetrate into the membrane such as blind branches. The walls of the channels have a spacing of 150 µm or less, and the proportion of the membrane surface area which comprises channels and/or branching structures having this spacing constitutes at least 50% of the total surface area of the membrane.

However, most of the aforementioned techniques for improving flow performance and total throughput of filter materials merely rely on increasing the applied area of filter material or have the drawback that the throughput is increased by incorporating channels penetrating through the entire membrane, whereby a desired filtration effect of retaining small contaminants to be removed from the filtrate cannot be achieved.

SUMMARY OF THE INVENTION

Thus, an object of the present invention is to provide a filter material capable to be used in the field of microfiltration which should have an improved total throughput and flow rate, without simply increasing the applied area of filter material in a filter device, as well as a simple and cost-efficient method for producing such a filter material.

The solution to the above technical problem is achieved by the embodiments characterized in the claims. In particular, the present invention provides a micro-porous filtration membrane, comprising a plurality of multi-level macroscopic discrete cavities extending from a first main surface of the membrane into the porous membrane, and being irregularly arranged within the membrane, wherein the average penetration depth of the cavities into the membrane is from 30 to 80% of the thickness of the membrane.

The pore size, i.e. the size of the micropores, of the micro-porous membrane according to the present invention is from about 0.08 to about 20 µm, preferably from 0.1 to 15 µm, and more preferably from 0.2 to 10 µm. The pore size is the diameter of the mean flow pore detected by a capillary flow porometer analysis with the capillary flow porometer by Porous Materials Incorporated, 20 Dutch Mill Road, Ithaca, N.Y. using a Solvay Galden HT55 16 dyne/cm wetting fluid. Thus, the micro-porous filtration membrane according to the present invention refers to a liquid-permeable membrane.

Within the present invention, the term "multi-level" is understood that the penetration depth of the plurality of cavities within the porous membrane is not uniform. That means, the penetration depths of the individual cavities may differ from another.

Further, the term "irregular", or any derivative thereof as used herein, is intended to describe a shape which is not an evenly-formed geometric shape such as a circle, rectangle, parallelepiped, etc., or an arrangement which does not follow a specific pattern, wherein objects are aligned in terms of being evenly-spaced apart, both laterally and longitudinally, or any iterative pattern.

In another aspect, the present invention relates to a method for producing the micro-porous filtration membrane according to the present invention, comprising the following steps:

providing a micro-porous filtration membrane having a first and second main surface, and modifying the first main surface of the membrane so as to mechanically, chemically and/or thermally form a plurality of multi-level macroscopic discrete cavities extending from a first main surface of the membrane into the porous membrane.

The micro-porous filtration membrane according to the present invention can be used in sterilizing processes such as food and beverage filtration of water, wine, beer or biopharmaceutical filtration of cell and bacteria nutrition media or clarification and purification filtration of cell and bacteria broths.

According to the present invention, the flow and total throughput of a given filter material can be improved not only by a larger filter area as such, but also by increasing the non-filtrate surface area and accessibility of the sub surface pores for filtration, so that more efficient filter materials are generated. In particular, a three dimensional surface which extends into the filter material creates voids, where formerly filter material has been present. Hence a lower flow resistance or vice versa higher flow rate can be achieved. In particular, due to different cavity heights, diameters and distances, the method of the present invention can affect several retentive layers of a membrane, reaching a higher cavity density. This results in an improved total throughput and flow rate, respectively.

Thus, in another aspect, the present invention further relates to a method for improving the throughput and/or flow rate of a micro-porous filtration membrane, comprising the step of modifying a first main surface of the membrane so as to mechanically, chemically and/or thermally form a plurality of multi-level macroscopic discrete cavities extending from a first main surface of the membrane into the porous membrane, and being irregularly arranged within the membrane, wherein the average penetration depth of the cavities into the membrane is from 30 to 80% of the thickness of the membrane.

DESCRIPTION OF THE DRAWINGS

The present invention will be described in more detail herein-below with respect to the following embodiments along with the accompanying drawings, wherein.

DESCRIPTION OF THE INVENTION

Figure 1:
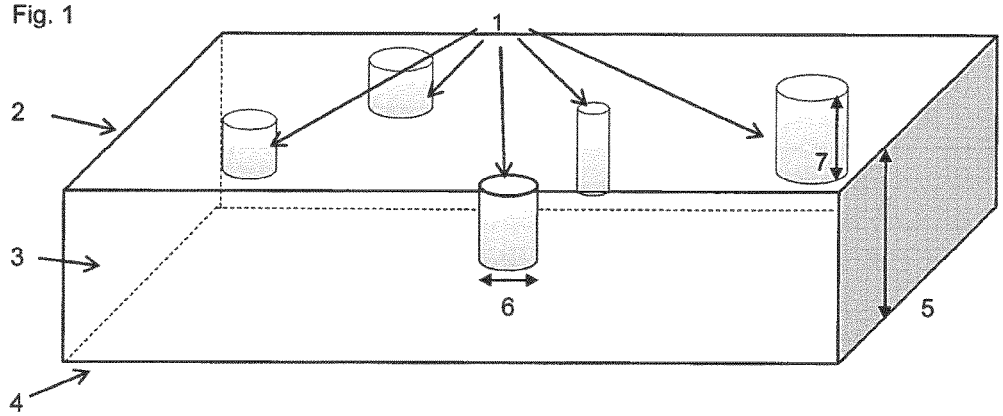
FIG. 1 illustrates diverse multi-level cavities in a micro-porous membrane with cavities having openings on the non-filtrate side and bottoms ending in multiple levels within the thickness of a micro-porous membrane.

According to the present invention, the micro-porous filtration membrane comprises a plurality of multi-level macroscopic discrete cavities which are irregularly arranged within the membrane, wherein the average penetration depth of the cavities into the membrane is from 30 to 80% of the thickness of the membrane. The macroscopic cavities extend from a first main surface of the membrane (i.e. non-filtrate side or upstream side) into the porous membrane. That means, according to the present invention, the cavities comprise a first end representing the opening on the first main surface of the membrane and a second end opposite to the first end that opens in the first main surface of the membrane, which is embedded within the membrane. Thus, the cavities extend from the first main surface of the membrane towards the second main surface of the membrane opposite to the first main surface.

The first main surface may be substantially parallel to the second main surface of the membrane (i.e. the deviation between the planes is less than 5°). Accordingly, the thickness of the membrane refers to the average distance of the first main surface to the second main surface of the membrane. In this context, it should be noted that the macroscopic cavities, which may be hereinafter also referred to as "cavities" differ from the micropores constituting the micro-porous membrane. Further, the term "discrete" is meant that the cavities are separated from each other and are not in the form of e.g. branched channels or network-like structures.

The macroscopic cavities present in the membrane according to the present invention can have various shapes and forms. For example, the cross-sectional profile of the cavity, particularly at the first end, may be circular, oval, rectangular, triangular, any higher polygon, or even any irregular shape. If the cross-sectional profile of the cavity is for example circular, the cavity thus may have a cylindrical, cone or frustum-like shape. Typically, the second end of the cavity may be tapered or rounded.

According to a preferred embodiment, the cavities have a cylindrical, cone, or pyramidal shape including the shape of a tetrahedron, square, pentagonal, hexagonal and star pyramid. According to the present invention, the basic shape of the cavities may be the same within the membrane or may differ from another. Among said shapes, a cylindrical shape in which the second end of the cavity may be tapered or rounded is particularly preferred.

The orientation of the cavities in the micro-porous membrane is not particularly limited. However, the cavities are preferably arranged so that the longitudinal axes thereof are substantially parallel (i.e. the deviation between the axes is less than 5°).

According to the present invention, the macroscopic discrete cavities extend from the first main surface of the membrane into the porous membrane towards the second main surface, wherein the average penetration depth of the cavities into the membrane is from 30 to 80% of the thickness of the membrane. That means, the second end of the cavity is embedded within the porous membrane at an average penetration depth of 30 to 80% with respect to the thickness of the membrane. The penetration orientation of the cavities is preferably perpendicular to the main surfaces of the membrane or within an angle of 45° or more, more preferably 60° or more, most preferably 75° or more, with respect to the main surfaces of the membrane. That means, the cavities are preferably formed so that their longitudinal axes are perpendicular to the main surfaces of the membrane, or within an angle of 45° or more, more preferably 60° or more, most preferably 75° or more, with respect to the main surfaces of the membrane.

According to a preferred embodiment of the present invention, the individual diameter of the cavities is from 0.1 to 1000 μm, more preferably from 1 to 500 μm, even more preferably from 10 to 500 μm. In this regard, it should be noted that the individual diameter of the cavities refers to the diameter of the cavity measured at the first end of the cavity, i.e. at the opening of the membrane's surface, as determined by the value of the horizontal diameter ($d_x$) and the vertical diameter ($d_y$). Thus, the term "individual diameter of the cavities" used within the present invention refers to the dimension of each cavity at the opening of the membrane's surface obtained from the value of $d_x$ and $d_y$.

As mentioned above, the cavity has preferably a cylindrical shape in which the closed bottom end (second end) of the cavity may be tapered or rounded. In such a case, the diameter of the cavities is substantially the same throughout 50%, more preferably throughout 75% of the penetration depth, i.e. the deviation of the diameter ranges between 10% and 40%, more preferably between 15% and 35% and most preferably between 20% and 30%. To determine the size of the macroscopic cavities including the individual diameter thereof and penetration depth, scanning electron microscopy (SEM) is employed.

In particular, the determinations of $d_x$ and $d_y$ were done by using a scanning electron microscope Quanta FEG 200 from Company FEI. To generate SEM pictures (FIGS. 4, 5, and 7 to 9) a high-vacuum pump and a secondary electron detector were used in addition. Each picture was taken at individual magnification in order to achieve the best quality for evaluation of geometrical data.

The captured pictures were then uploaded in a software called Scandium (v.5.2) from company Olympus Soft Imaging Solutions GmbH. Before measuring, the software was calibrated to each used magnification. The dimensions $d_x$ and $d_y$ were then examined at the opening of a cavity, where $d_x$ was the diameter in horizontal direction (biggest span from left to right) and $d_y$ the diameter in vertical direction (biggest span from up to down, see FIG. 4(f)). The position of the sample was random, which means measurement of $d_x/d_y$ was only based on the orientation of a cavity within the SEM picture.

According to the present invention, the individual diameter of the cavities present in the micro-porous membrane may be substantially the same for each of the plurality of cavities. However, according to a particularly preferred embodiment of the present invention, the individual diameter of the cavities present in the micro-porous membrane is not uniform. That means, the individual diameter of each of the plurality of cavities is preferably not the same, but within a specific deviation. In particular, according to the present invention, the individual dimensions $d_x$ and $d_y$ preferably show a standard deviation of more than 10%, preferably 11% or more, more preferably 15% or more and most preferably 20% or more from the respective arithmetic mean of the cavity diameters $d_x$ and $d_y$ (see also Tables 2 and 5 of Examples 1 and 2 described herein-below). According to a particularly preferred embodiment of the present invention, the dimensions of the individual diameter of the cavities have a standard deviation of 20% or more from the arithmetic mean of the cavity diameters.

The upper limit of the standard deviation for the dimensions $d_x$ and $d_y$ of the cavities is not particularly limited. However, the deviation is preferably in the range of 100% or less, more preferably 75% or less, and most preferably 50% or less.

According to the present invention, the portion of the macroscopic cavities in the micro-porous membrane may be adjusted depending on the intended use of the membrane. In particular, the percentage of the area of the macroscopic cavities on the first main surface of the membrane, which can be also referred to as the "surface porosity", is preferably at least 1%, more preferably at least 5%, even more preferably at least 10%, and most preferably at least 15%. Since the structural strength of the resultant membrane decreases with an increased surface porosity, the surface porosity is preferably 80% or less, more preferably 70% or less, even more preferably 60% or less, and most preferably 50% or less. According to a particularly preferred embodiment of the present invention, the surface porosity is from 15 to 50%.

According to the present invention, the material used to form the micro-porous membrane is not particularly limited. For example, the membrane may be formed using a porous polymer membrane made from polyether sulfone (PESU) or polyamide (PA) or a cellulose derivative, such as cellulose mixed ester, cellulose acetate, cellulose nitrate or cellulose, or polypropylene (PP) or polyethylene (PE) or polytetrafluoroethylene (PTFE) and/or expanded polytetrafluoroethylene (ePTFE) or polyvinylidene difluoride (PVDF) or polyvinyl chloride (PVC). The filter material may also be formed using mineral or polymer fiber filtration media or bonded and/or non-bonded non-wovens, such as spunlaids or melt-blown spunlaids or staple fiber webs or carded webs (either calendered or non-calendered), or using cellulose, polyamide (PA), expanded polytetrafluoroethylene (ePTFE), ethylene-tetrafluorethylene (ETFE), polyether ether ketone (PEEK), polyether sulfone (PESU), polyphenylensulfide (PPS) or polyester or polyolefins, such as PE or PP, or glass fibers or glass microfibers. In addition, it is possible for the filter material to be formed using a fabric or an extruded net made of at least one of the aforementioned polymers.

Moreover, according to the present invention, it is possible that the filter material is formed using a functionalized porous filtration medium, such as a modified polymer membrane made of polypropylene (PP), polyethylene (PE), polyvinylidene difluoride (PVDF), polyamide (PA), expanded polytetrafluoroethylene (ePTFE), polyether sulfone (PESU), cellulose acetate (CA) or cellulose nitrate (CN).

Depending on the filter material used to form the micro-porous membrane, the membrane according to the present invention may be rigid or flexible. Furthermore, depending on the desired use of the membrane, it is possible that the membrane according to the present invention is formed so as to be used for dead-end filtrations, such as a flat membrane plate (i.e. disc like), or for cross-flow filtrations, according to which the membrane may be in form of spiral wounds or hollow fibers.

Preferably, the micro-porous membrane is a porous polymer membrane made from polyether sulfone (PESU) or polyamide (PA) or polyvinylidene difluoride (PVDF) or a cellulose derivative. The micro-porous membrane according to the present invention may be also made of a combination of the aforementioned materials.

As mentioned above, the micro-porous membrane according to the present invention may be composed of a single membrane layer or comprised of at least two different layers of membrane material. Preferably, the micro-porous membrane contains at least two different membrane layers having different pore sizes such that the first layer to be passed by the feed has a larger pore size compared to the second membrane layer. In particular, according to the present invention, the micro-porous membrane may include several retentive layers, according to which at least one layer made of a porous or micro-porous matrix material is provided on the non-filtrate side area of the membrane, and at least one layer made of a micro-porous matrix material is provided on the filtrate side area of the membrane.

According to the present invention, the average penetration depth of the macroscopic discrete cavities into the membrane is from 30 to 80%, preferably from 35 to 70%, even more preferably from 40 to 60% of the thickness of the membrane. In this context, it should be noted that the thickness of the membrane refers to the total thickness of the micro-porous membrane having the plurality of multi-level cavities. That means, in case the micro-porous filtration membrane comprises for example two distinct membrane layers having e.g. different pore sizes, of which only one of said layers comprises the multi-level macroscopic cavities, the thickness of the layer not having the cavities is not considered in this respect.

The thickness of the micro-porous membrane according to the present invention may be adjusted on the intended use and can range from 10 μm to 5 mm. Preferably, the thickness of the membrane is from 10 μm to 1000 μm, more preferably from 20 μm to 500 μm. The thickness of the membrane can be measured by a thickness gauge ("Messtaster", Type J100 or J200, precision 0.001 mm, from Hahn and Kolb, Stuttgart, Germany).

In another aspect, the present invention further relates to a method for producing the micro-porous filtration membrane according to the present invention, comprising the following steps:

providing a micro-porous filtration membrane having a first and second main surface, and modifying the first main surface of the membrane so as to mechanically, chemically and/or thermally form a plurality of multi-level macroscopic discrete cavities extending from a first main surface of the membrane into the porous membrane.

To produce the micro-porous filtration membrane according to the present invention, the equipment and devices and machinery conventionally used for the production of membrane filters may be used, saving costs for additional or specific equipment and devices. In particular, according to the present invention, the step of providing the micro-porous filtration membrane can be carried out by conventional methods known in the art.

According to the present invention, such micro-porous structures, preferably in terms of micro-porous polymeric membranes, are treated at their first main surface, i.e. non-filtrate surface, by mechanical, chemical and/or thermal methods in order to extend the non-filtrate surface by creating additional surface by multi-level cavities. According to the present invention, the step of modifying the first main surface of the membrane is not particularly limited as long as a plurality of multi-level macroscopic discrete cavities extending from the first main surface of the membrane into the porous membrane having an average penetration depth of from 30 to 80% of the thickness of the membrane can be achieved. However, as mentioned above, according to the present invention, the plurality of multi-level macroscopic discrete cavities with individual diameters $d_x$ and $d_y$ are irregularly arranged within the membrane.

Preferably, the step of modifying the first main surface of the membrane is carried out by spiking using a plurality of sharp needles. In particular, cavities of varying diameter and depth as schematically shown in FIG. 1 can be created by applying, for example, a fixed bundle of needles with defined pressure to the non-filtrate surface of the micro-porous structure. The large number of needles forms a plane of sharp spikes with their sharp tips. Preferably, the tip of the needle is very sharp, i.e. the diameter of the tip is preferably 100 μm or less, and even more preferably 50 μm±20 μm, upon which the needle can easily cut into the micro-porous structure.

According to the present invention, the geometry of the needle tips is determined using SEM. The procedure employed is the same as for determining the diameters $d_x$ and $d_y$ of a cavity with exception to the method to measure the tip diameter via Scandium software. Here, software is again calibrated according to the used magnification. If the ending of the needle tip does not have a spherical shape but is in form of an obtuse taper, the diameter of the needle tip is determined by measuring the smallest vertical diameter of the obtuse taper, as it is shown in FIG. 9(b) (see the fine white line in FIG. 9(b)). If the ending of the needle tip has a spherical shape, a circle is fitted to that shape. The diameter of this circle is taken as the tip diameter, as it is shown in FIG. 9(a).

Thus, according to the present invention, it is preferred that the step of modifying the first main surface so as to form the cavities is carried out in such a way that the micro-porous structure of the membrane is substantially not affected at all. That means, according to the present invention, the micro-porous structure is substantially not compressed, whereby the tendency that the membrane may be blocked or that the flow rate may be reduced can be minimized.

Besides spiking using a plurality of sharp needles, according to the present invention, the step of modifying the first main surface of the membrane, so as to form the cavities, may be also carried out by other mechanical techniques, such as drilling.

As mentioned above, next to mechanically forming the cavities, it is also possible to form the cavities by employing thermal or chemical processes capable of forming the cavities. For example, the cavities may be thermally formed using laser ablation techniques. In particular, it is possible to use laser drilling or laser polishing, so as to form the cavities. Results of this technique are given in Example 3. In Example 3 described herein below, a laser ablation was used in a kind that a femto second laser (Manufacturer/Type Light Conversion Pharos, built year 2013) drilled heterogeneous cavities into the surface of the desired membrane. Two kinds of membranes were used—polyether sulfone micro filtration membrane type 15445 (prototype version) and cellulose acetate membrane type 18357. Cavities with various penetration depths were drilled into the membrane structure, while a general minimum drilling depth of 30% of the overall membrane depth was achieved. In order to reach a high cavity density on the membrane surface, the following pattern was used for the ablation:

Vectors of different length were arranged in parallel lines to create an area of a quarter circle with d=47 mm. Cavities were created while the laser ran along those predefined lines by using a galvo scanner. The writing speed of the scanner was 2500 mm/s. In combination with the pulse frequency of the femto second laser the distance between each cavity on a vector resulted in 25 μm. The distance between the vectors (jump distance) was also adjusted to 25 μm. That resulted in same distances between neighbored cavities. After finishing one quarter area of a circle the method was repeated. The repetition runs are dependent of the membrane type and desired cavity depth. With the end of the repetition run the sample table turns 90° and the above-mentioned procedure repeats until a full area circle has been generated.

TABLE 1

| Membrane Type | Laser Entry Voltage | Number repetition runs/ Pulses per Cavity | Desired Cavity Depth |
| --- | --- | --- | --- |
| CA 18357 | 610 V | 3 | 50 μm |
| PES 15445 (prototype) | 510 V | 5 | 50 μm |

In addition, according to the present invention, the cavities may be also formed by track etching, by which energetic heavy ions cause the formation of damaged tracks across the irradiated membrane material, which are subsequently treated by wet chemical etching.

According to the present invention, the flow and total throughput of a given filter material can be improved not only by a larger filter area as such, but also by increasing the non-filtrate surface area and accessibility of the sub surface pores for filtration, so that more efficient filter materials are generated. In particular, a three dimensional surface which extends into the filter material creates voids, where formerly filter material has been present. Hence a lower flow resistance or vice versa higher flow rate can be achieved. In particular, due to different cavity heights, diameters and distances, the method of the present invention can affect several retentive layers of a membrane, reaching a higher cavity density. This results in an improved total throughput and flow rate, respectively.

The present invention will be described in more detail herein-below with respect to the following non-limiting examples.

EXAMPLES

Performance Evaluation, Total Throughput and Flow Rate

Figure 2:
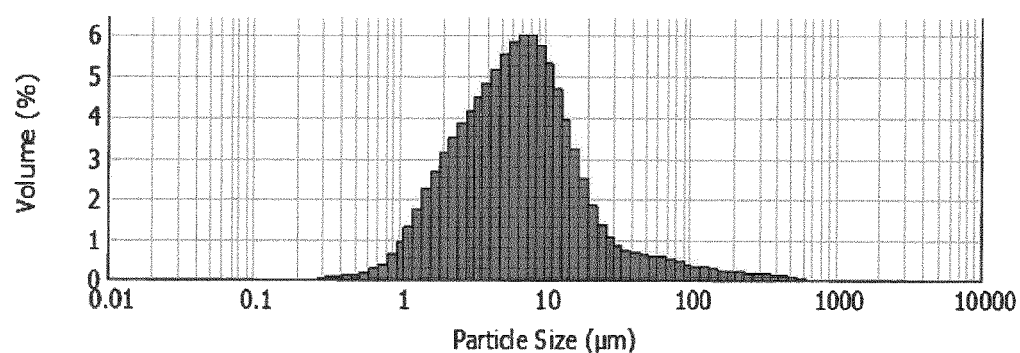
FIG. 2 shows a particle size distribution of a used model solution to evaluate performance of total throughput.

Total throughput performance was measured with help of a particulate model solution, particle distribution as shown in FIG. 2. Ingredients of this solution are mainly carbohydrates, lipids and particles of malt, barley and rye. The test skid consists of a balance, pressure sensor, pressure vessel and a filter holder. A connected software calculated current flow and blocking of the tested filter. The model solution was filtered through the membranes at a constant pressure of 1 bar. A test was finished when the membrane filter or filter combination reached a blocking of 93 to 95%. This refers to 5 to 7% of initial/maximum flow, whereby flow was measured as a function of filtrate mass per time. The theoretical maximum filterable amount (Vmax) was calculated by regression (implemented in software). Vmax according to the invention is the theoretical maximum throughput calculated by regression to a throughput curve (weight over time) at 7 or 5% flow, respectively, of the initial flow. The software which was used for data collection and as well for Vmax determination is called LimsMultiStandzeit. It is a Sartorius intern Software version 1.3.06.

Flow performance was measured by using the same test skid as described above. RO (reverse osmosis) water was filtered at a constant pressure of 1 bar for 1 min through a 47-mm filter disc. The resulting filtration volume leads to flow performance given as "Flow Rate" in ml/min (see Table 4).

Filter Materials

The following evaluations were made by using a combination of polymeric phase inversion membranes using hydrophilic polyether sulfone as the basis polymer, the pre-filter type 15445 and final or main filter type 15407, both commercially available from Sartorius Stedim Biotech GmbH, Germany. A polymer solution was spread on a support; the membrane side formed facing this belt is called belt side. The types 15445/15407 are specified with a thickness from 145 to 175 and 140 to 160 µm, respectively, and a nominal pore size of 0.5 µm and 0.2 µm, respectively. Membranes were tested so that the belt side was facing the non-filtrate (upstream) side. Here, both discs were wetted with RO water and stacked one upon the other and sealed within a disc filter holder.

Example 1—Diverse Multi-Level Cavities

A micro-porous polymeric membrane was modified in such a way that its specific surface area was increased. This was achieved by spiking the non-filtrate side of a membrane (see. FIG. 1, ref. 2), with the resulting cavities (see FIG. 1, ref. 1) ending in 30 to 80% of the membrane's thickness (see FIG. 1, ref. 5). In this particular case, the specific area of the membrane should be taken as the surface of the upstream area (see FIG. 1, ref. 2) and a cylinder's inner surface area without the correspondent lid surface corresponding to the cavities. Consequently the specific surface area is dependent from inner diameter as well as height of the cavities.

The specific surface area has been determined using the following equation and by analysis of SEM cross sections of several cavities, upon which the mean cavity height has been evaluated.

$$\text{Specific surface area} = \pi/4 \cdot d^2 + \pi \cdot d \cdot h + A = \pi \cdot d\left(\frac{d}{4} + h\right) + A,$$

where A=membrane surface (13 cm²), h=height of a cavity; d=average of all $d_x$ and $d_y$ expressed by the following equation $$d = \frac{\left(\sum_1^n d_{x,n} + \sum_1^n d_{y,n}\right)}{2n}.$$

A representative SEM picture showing the height of a cavity which was used for the calculation of the specific surface area is shown in FIG. 7(e).

Figure 3:
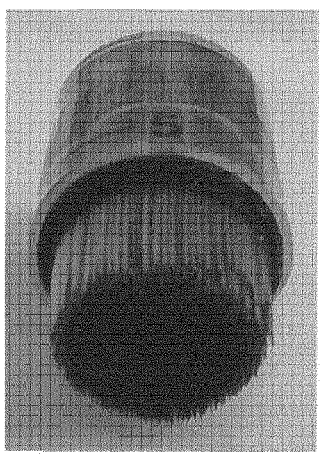
FIG. 3 shows a stamp of needles which are arranged, so that the tips form a circular plane.

The spiking was done with a stamp (see FIG. 3) with a diameter of 1.7 cm, including approximately 800 needles of different types arranged in a circular way and fixed by an epoxide resin. The needle tips are arranged in a plane for the contact with non-filtrate side of the membrane. The spiking was done with a weight of 530 g on the stamp additional to the stamp's weight itself (39 g), which refers to a pressure of about 416 N/m². The stamping was done over the whole non-filtrate side area of a 47-mm disc of a membrane. The deviation of needle tip diameters results in cylindrical cavities having an arithmetic mean of the horizontal diameter (±standard deviation), $d_x$, of 59.8 µm±12.6 µm and an arithmetic mean of the vertical diameter (±standard deviation), $d_y$, of 57.8 µm±14.0 µm (see FIG. 4(a)-(e), and Table 2).

TABLE 2

| cavity | Diameter cavities by needle stamp | |
|---|---|---|
| | $d_x$ [µm] | $d_y$ [µm] |
| 1 | 60 | 57 |
| 2 | 78 | 76 |
| 3 | 65 | 67 |
| 4 | 47 | 42 |
| 5 | 49 | 47 |
| arithmetic mean | 59.8 | 57.8 |
| STDEV | 12.6 | 14.0 |
| STDEV in % | 21.13 | 24.20 |

STDEV: standard deviation
STDEV in %: standard deviation in % from arithmetic mean Moreover, this deviation results in a penetration of the porous membrane's thickness of 30 to 80%. Due to the heterogeneous distribution of needles within the generated circular plane of the stamp, the resulting spikes are also not homogeneously distributed, which means the distances between cavities are random (see FIG. 5).

The potential of this method is given in the following Table 3 showing the theoretical maximum throughput (Vmax) of a particulate model solution determined at a flow≤5% of initial flow. Here, the micro-porous polymeric membrane combination of types 15445 and 15407 was tested. Both combinations, treated and untreated, were taken from same membrane lots and rolls. Only the pre-filter-membrane 15445 was spiked, whereas the main filter membrane 15407 was not spiked.

In this context, the average values of two measurements of micro-porous polymeric membranes 15445 and 15407 in a two layer stack were determined.

These were tested in reference to an untreated membrane combination of types 15445 and 15407, the result of which is given in Table 3, line 1 'Ref. sample'. The column "benefit to ref." indicates the enhancement in Vmax of each sample in view of the reference sample in percent. The membrane combination translates into a benefit of maximum 31% compared to the reference sample. Besides, it was observed that flow rate benefits from that modification, too. A 13% better flow rate was achieved by using the spiked membrane combination compared to the untreated reference sample (see Table 4).

TABLE 3

| Trial | structure used | total through-put [g] | Vmax [g] | upstream area [cm$^2$]** | Vmax STDEV* [g] | benefit to ref. [%] |
|---|---|---|---|---|---|---|
| 1 | Ref. sample | 71 | 91 | 13 | 4 | 0 |
| 2 | 10× spiked | 85 | 111 | 13 | 6 | 22 |
| 3 | 20× spiked | 94 | 119 | 13 | 16 | 31 |

*STDEV = standard deviation
**based on 47-mm filter disc
"10× spiked": 10 times spiked with needle stamp over whole membrane area
"20× spiked": 20 times spiked with needle stamp over whole membrane area

TABLE 4

| | | Flow Rate at 1.0 bar pressure (ml/min) | | | | | | |
|---|---|---|---|---|---|---|---|---|
| Trial | structure used | T1 | T2 | T3 | T4 | T5 | AVERAGE | STDEV | benefit to ref. [%] |
| 1 | Ref. sample | 191 | 196 | 197 | 207 | 198 | 198 | 6 | 0 |
| 2 | 20× spiked | 220 | 224 | 217 | 230 | 224 | 223 | 5 | 13 |

Moreover, it was examined that the throughput value increases by increasing the number of spikings. Membrane combination with "10× spiked" membrane 15445 reached a considerable benefit of 22% in terms of Vmax compared to the untreated reference sample. The "20× spiked" membrane for which the spiking rate was doubled showed even better results (31% Vmax increase) as compared to the reference sample.

Example 2—Comparative Example: Homogeneous Spiking Pattern

In Example 2, representing a comparative example, a membrane was modified by spiking the non-filtrate side (see FIG. 1, ref. 2) with the resulting cavities (see FIG. 1, ref. 1) ending in approximately 50% of the membrane's thickness (see FIG. 1, ref. 5).

The specific surface area has been determined using the following equation and by analysis of SEM cross sections of several cavities, upon which the mean cavity height has been evaluated.

$$\text{Specific surface area} = \pi/4 \cdot d^2 + \pi \cdot d \cdot h + A = \pi \cdot d\left(\frac{d}{4} + h\right) + A,$$

where A=membrane surface (13 cm$^2$), h=height of a cavity; d=average of all $d_x$ and $d_y$ expressed by the following equation $$d = \frac{\left(\sum_1^n d_{x,n} + \sum_1^n d_{y,n}\right)}{2n}.$$

Figure 7:
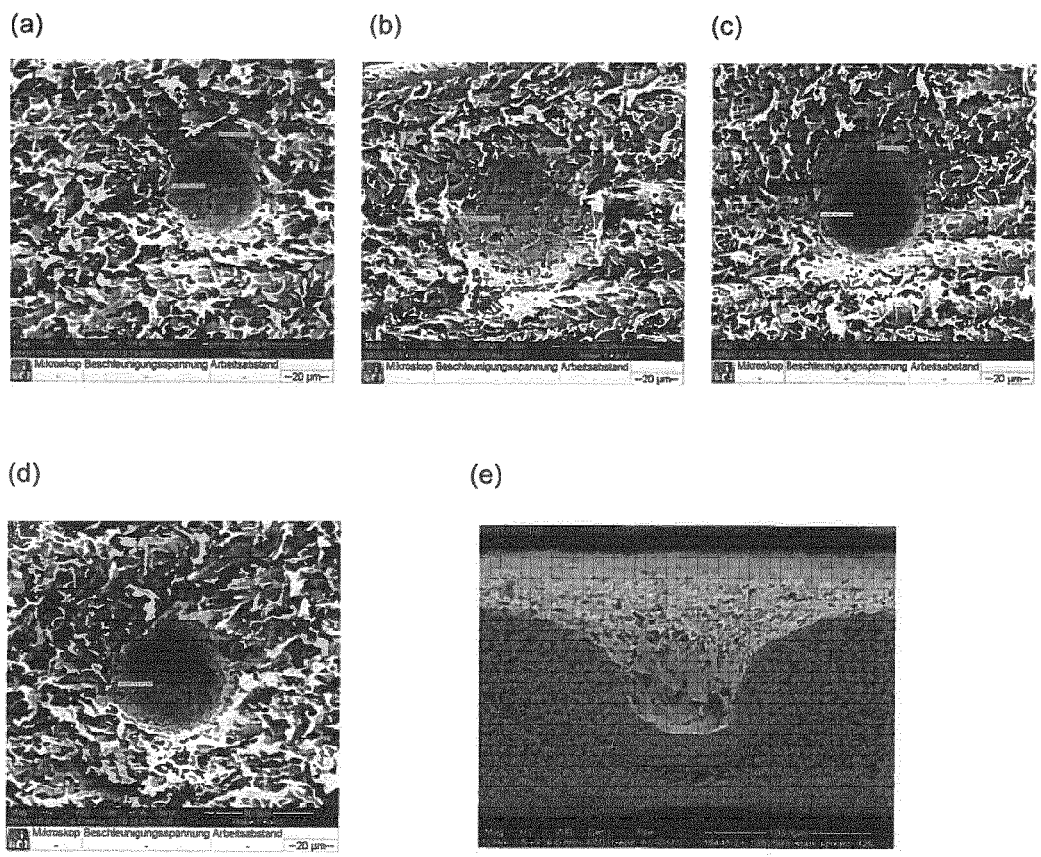
FIG. 7(a) to (e) show SEM pictures for analysis of dimensions and diversity of single cylindrical cavities; small deviation in diameters and penetration depth of sample 15445 according to Example 2.
Figure 8:
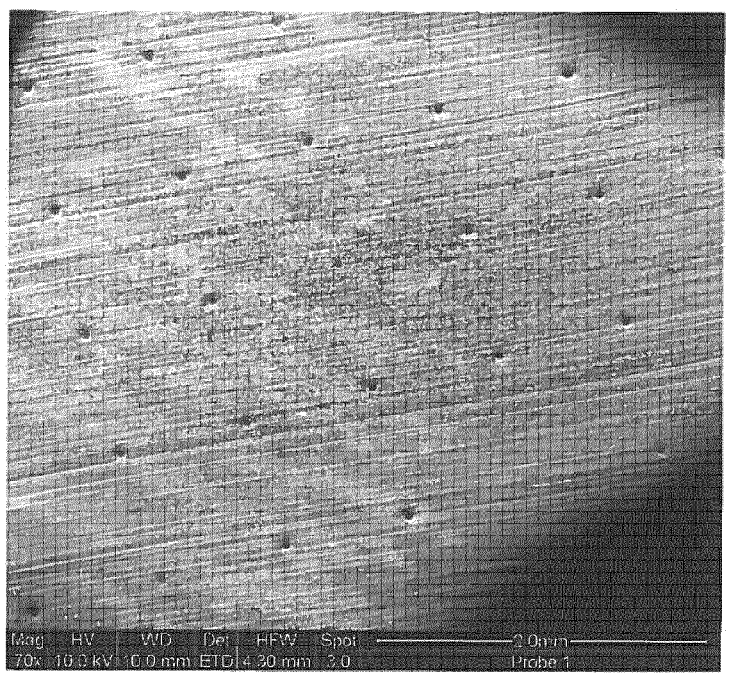
FIG. 8 shows the homogeneous distribution of cavities obtained in Example 2 (membrane sample 15445)
Figure 9:
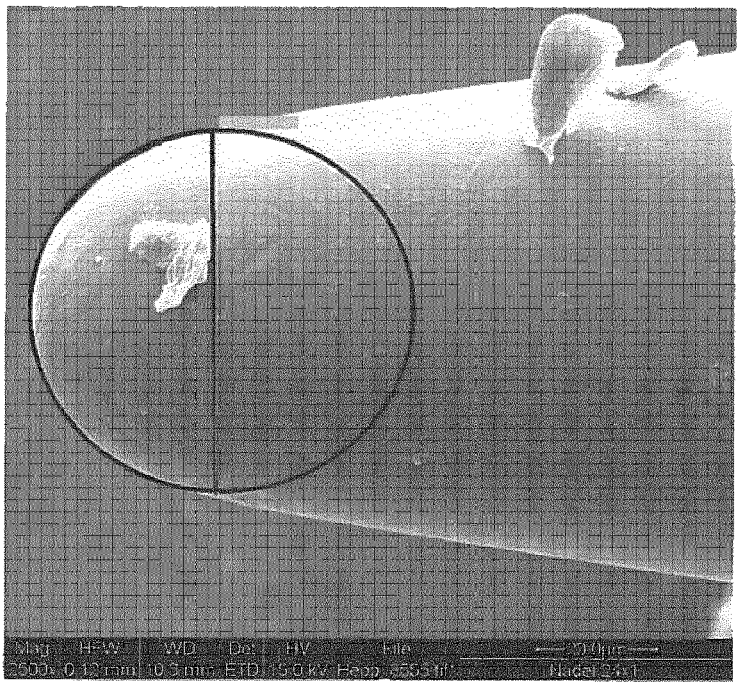
FIG. 9 shows different needle tips and how the geometry, i.e. the diameter thereof, has been determined with (a) having a spherical shape ending, and (b) having an obtuse taper ending.
Figure 9:
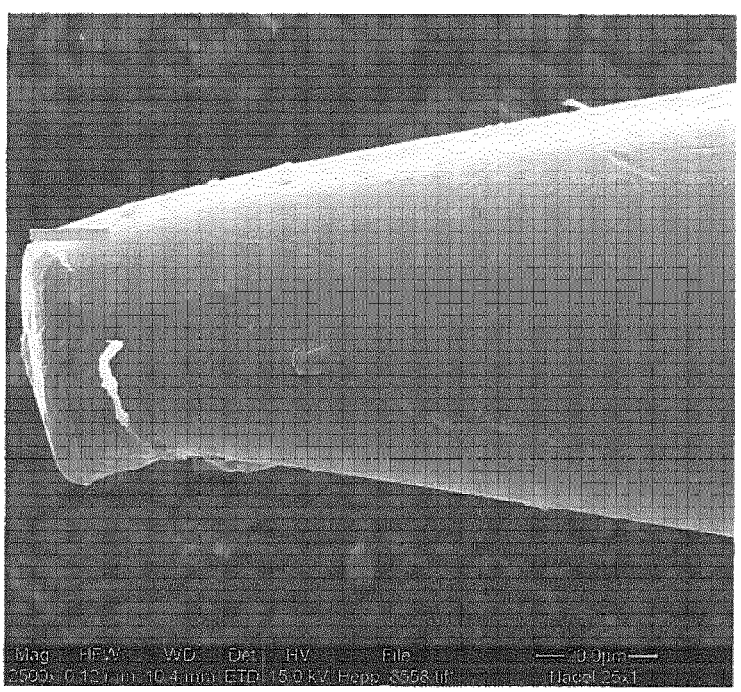

A representative SEM picture showing the height of a cavity which was used for the calculation of the specific surface area is shown in FIG. 7(*e*).

Figure 6:
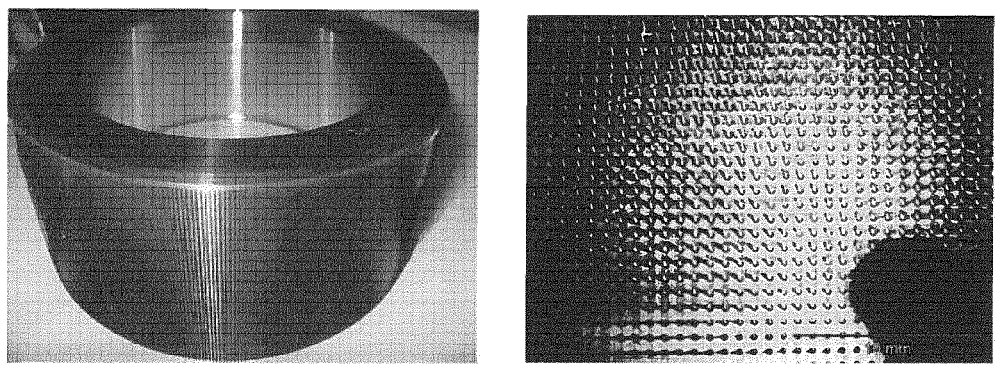
FIG. 6 shows a roll of needles, which are arranged like lines along the circumference with identical distances between each other, used in Example 2.

The difference between Example 2 and Example 1 resides in the fact that in Example 2, spiking was done with a needle roll (see FIG. 6) including approximately 26000 needles of the same type arranged in lines along the circumference of the roll with an outer diameter of 10.7 cm and a width of 5 cm. All needles have the same distance (approximately 0.8 mm) between each other, which results in a homogeneous spiking pattern (see FIG. 8). The spiking relies solely on the own weight of the roll (1650 g). The stamping was done by rolling the needle roll once or twice for trial Nos. 2, 3 and 4 over the whole surface of a 47-mm disc of a single membrane. The geometry of the needle tip resulted in cylindrical cavities having an arithmetic mean of the horizontal diameter (±standard deviation), $d_x$, of 53 µm±7.5 µm and an arithmetic mean of the vertical diameter (±standard deviation), $d_y$, of 55.6 µm±8.2 µm (see FIG. 7(*a*) to (*d*), and Table 5). Moreover, this resulted in a penetration depth of the membrane's thickness of approximately 50% (see FIG. 7(*e*)).

TABLE 5

| | Diameter cavities by needle roll | |
|---|---|---|
| cavity | $d_x$ [µm] | $d_y$ [µm] |
| 1 | 43 | 46 |
| 2 | 60 | 65 |
| 3 | 51 | 54 |
| 4 | 61 | 63 |
| 5 | 50 | 50 |
| arithmetic mean | 53 | 55.6 |
| STDEV | 7.5 | 8.2 |
| STDEV in % | 14.18 | 14.75 |

STDEV: standard deviation
STDEV in %: standard deviation in % from arithmetic mean In particular, similarly to Example 1, a combination of PES membranes (polyether sulfone types 15445 and 15407) was tested, in which only the pre-filter membrane 15445 was spiked. These were tested in comparison to an untreated structure. Both combinations were taken from same membrane lots and rolls.

The results of this method are given in the following Table 6, showing the values of Vmax of both combinations when filtering a particulate model solution based on the average values of three measurements.

TABLE 6

| Trial | structure used | total through-put [g] | Vmax [g] | upstream area [cm$^2$] | Vmax STDEV [g] | benefit to ref. [%] |
|---|---|---|---|---|---|---|
| 1 | Ref. sample | 43 | 48 | 13 | 2 | 0 |
| 2 | 1× spiked | 49 | 55 | 13 | 3 | 13 |
| 3 | 1× spiked | 47 | 54 | 13 | 0 | 12 |
| 4 | 2× spiked | 47 | 53 | 13 | 1 | 9 |

"1× spiked": once rolled with needle roll over whole membrane area
"2× spiked": twice rolled with needle roll over whole membrane area In this example, the standard deviation for $d_x$ and $d_y$ was 14.18% and 14.75%, respectively, and the benefit in terms of Vmax ranged between 9% and 13% increase compared to the reference sample.

In contrast to this Example 2, one can achieve much higher benefits in terms of Vmax (increase by 22% and 31%, respectively), if the standard deviation for $d_x$ and $d_y$ is much larger and amounts to 21.13% and 24.20%, respectively (see Example 1, Tables 2 and 3).

CONCLUSION

When comparing the results obtained in Example 1 and Example 2, the following relevant differences can be summarized.

Firstly, regarding the differences in pattern structure, since the comparative method uses a kind of repetitive pattern, the deviation in distances is quite low. That means, the use of an homogeneous pattern leads to a fixed density of cavities. On the other hand, for Example 1, due to heterogeneous arrangement of several needle types within a circular stamp and to multiple stamping of several areas of the desired membrane, the deviation of distances for this method is relatively high and results in a higher density of cavities.

Figure 4:
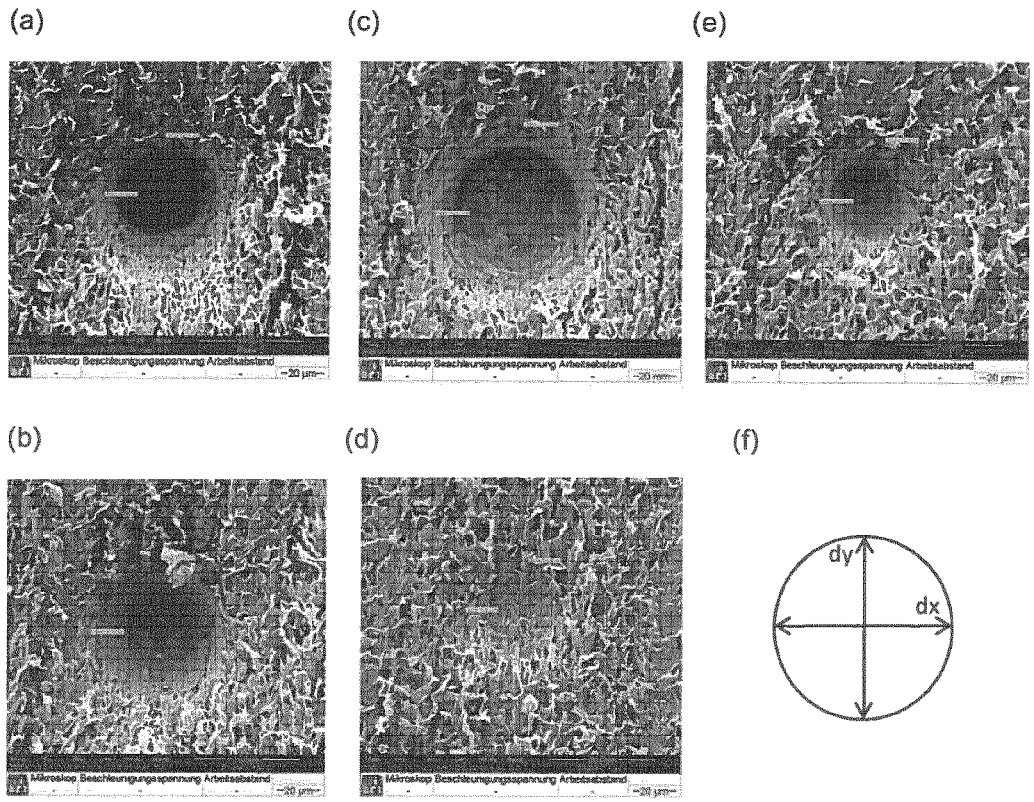
FIG. 4(a) to (e) show SEM (scanning electron microscopy) pictures for analysis of dimensions and diversity of single cylindrical cavities, differences in diameters and penetration depth of sample 15445 according to Example 1; (f) shows the measurement of cavities.
Figure 5:
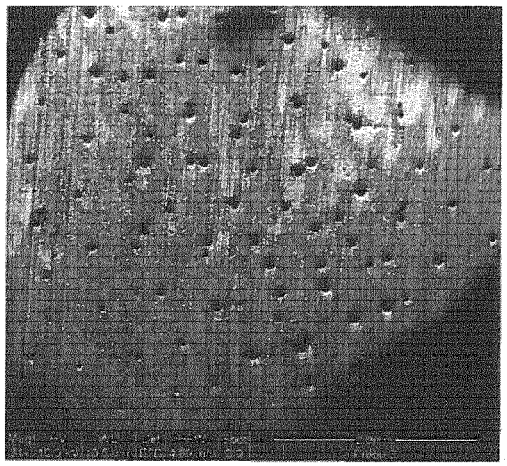
FIG. 5 shows the irregular (heterogeneous) distribution of diverse multi-level cavities of membrane sample 15445 according to Example 1.

Secondly, the needle tips of the comparative method are very similar to achieve homogeneous patterns. According to the present invention, different needle types are used and these vary in geometry. This results in much more deviated cavity diameters and heights (penetration depths) as it is shown in FIGS. 4 and 5 compared to FIGS. 7 and 8.

In addition, structural differences mentioned above result in different benefits compared to the reference membrane combination. Due to different cavity heights, diameters and distances, the method according to the present invention affects several retentive layers of a membrane, reaching a higher cavity density. This results in a maximum gain of throughput of 31% compared to the comparative method with a maximum gain of 13% (see respective maximum Vmax values of Table 3 and Table 6). Diverse cavity patterns in micro-porous membranes according to the present invention lead to more efficient filter membranes than those which patterns are done homogeneously according to Example 2.

Example 3—Cavities Generated by Laser Ablation

Figure 10:
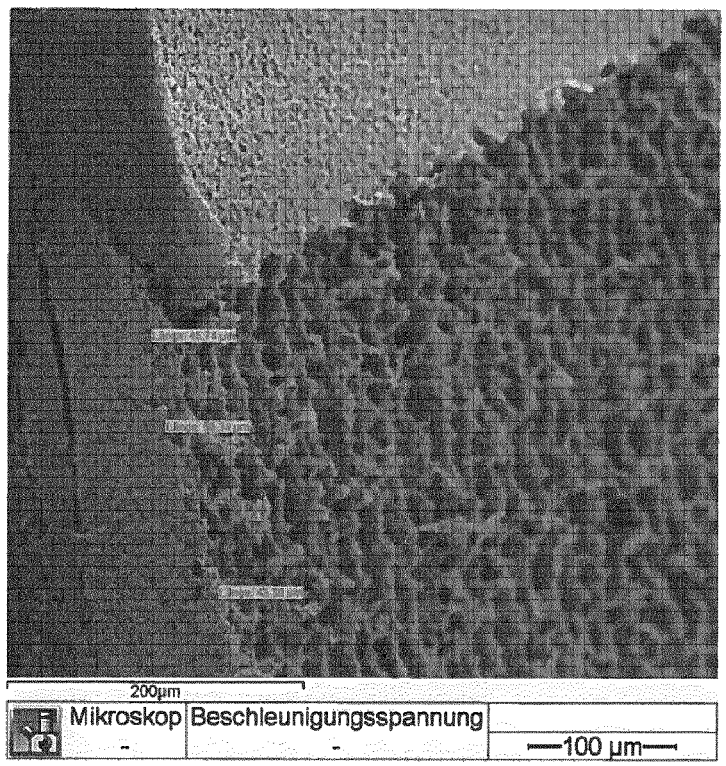
FIG. 10 and FIG. 11 show cavities generated on membrane type 18357 of Example 3.
Figure 11:
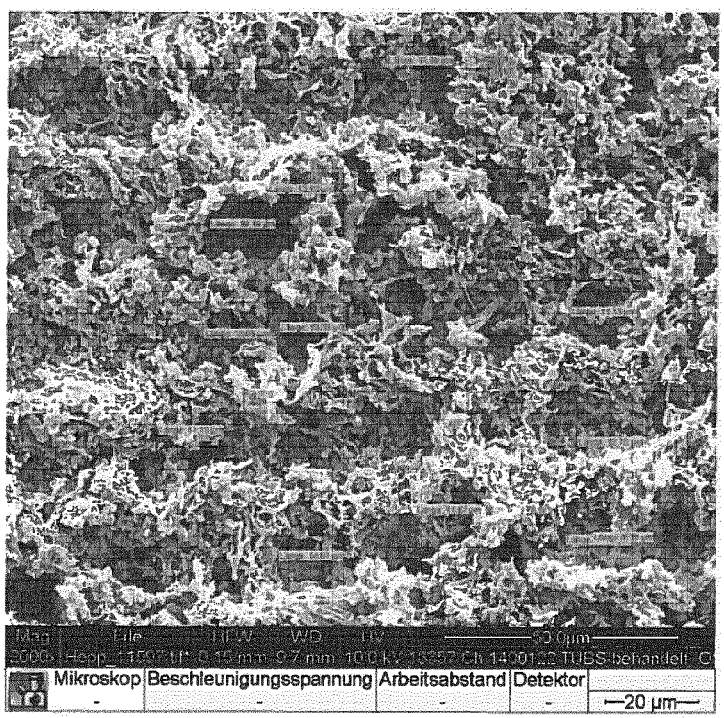
Figure 12:
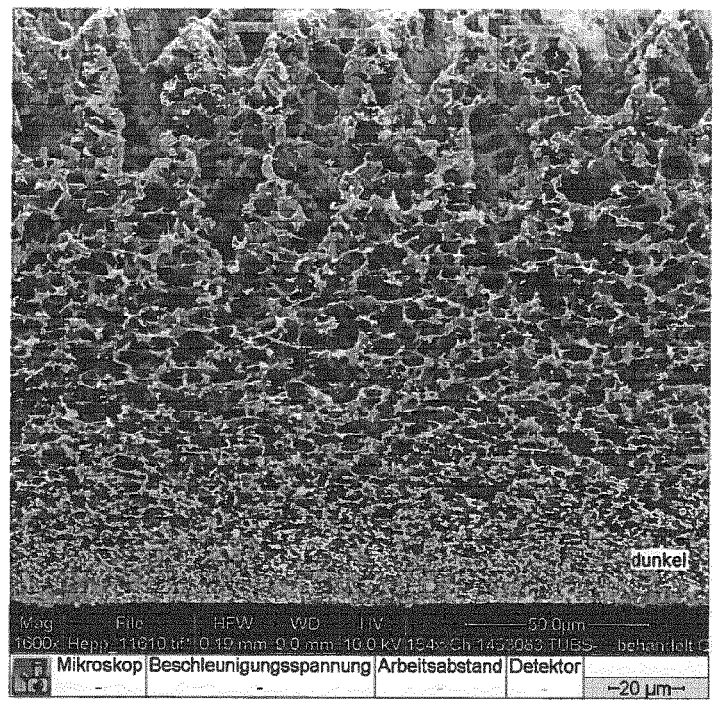
FIG. 12 and FIG. 13 show cavities generated on membrane type 15445 (prototype) of Example 3.
Figure 13:
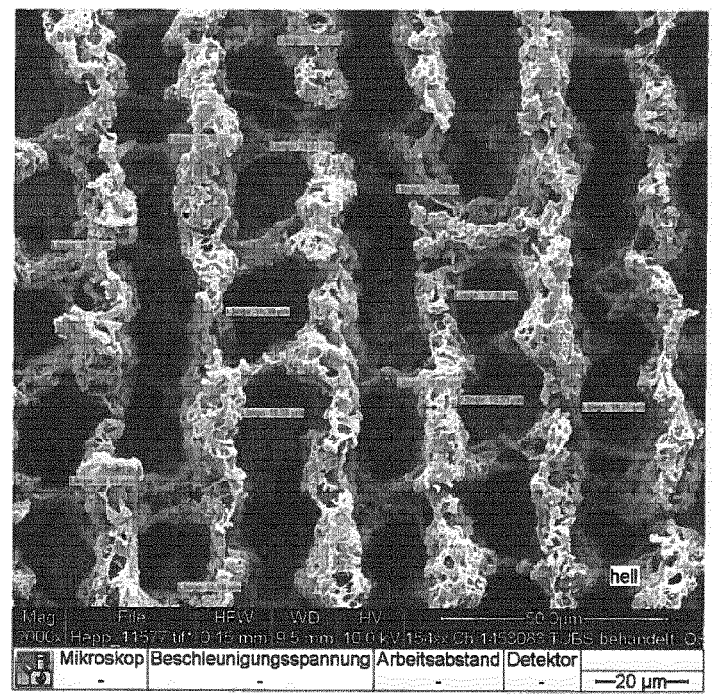

In Example 3 two kinds of microporous membranes were modified by laser ablation of the non-filtrate side. Multi-level cavities were generated by variation of the penetration depth of the cavities into the membrane structure. The geometrical properties of the cavities generated on membrane type 18357 are shown in FIGS. 10 and 11, those of type 15445 (prototype) in FIGS. 12 and 13. Moreover, the average geometrical numbers are given in Table 7. The average penetration depth was in both cases 50 μm, which refers to 30-40% of the membrane overall thickness.

TABLE 7

Diameter cavities by laser ablation

| cavity | 18357 | | 15445 (prototype) | |
| --- | --- | --- | --- | --- |
| | $d_x$ [μm] | $d_y$ [μm] | $d_x$ [μm] | $d_y$ [μm] |
| 1 | 18.1 | 10.7 | 18.38 | 18.97 |
| 2 | 10.6 | 13.5 | 19.55 | 22.94 |
| 3 | 10.4 | 11.1 | 18.23 | 37.2 |
| 4 | 11.1 | 12.8 | 18.23 | 16.61 |
| arithmetic mean | 12.55 | 12.025 | 17.06 | 19.85 |
| STDEV | 3.7 | 1.3 | 18.29 | 23.114 |
| STDEV in % | 29.58 | 11.14 | 0.9 | 8.2 |

Figure 14:
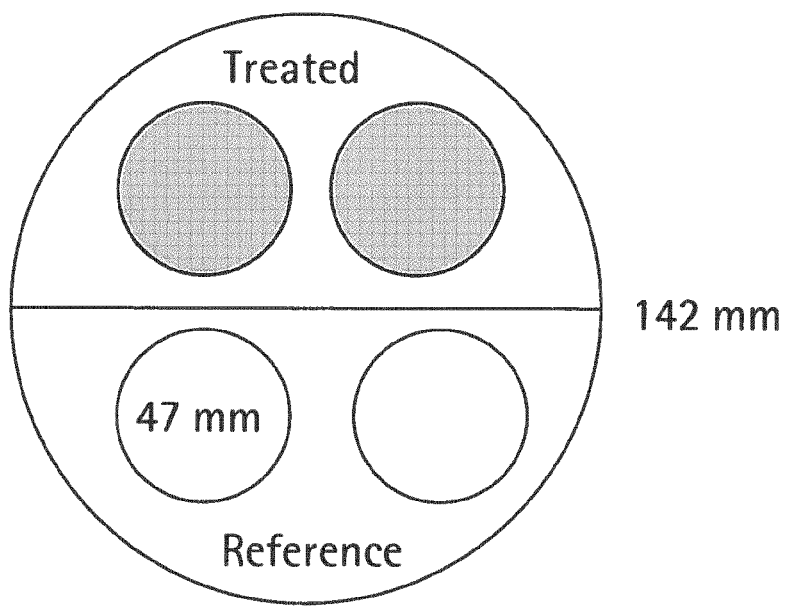
FIG. 14 illustrates sample preparation of Example 3.

The samples for performance comparison were prepared as follows. On a 142 mm diameter disc filter of the desired membrane type, two circle areas with a diameter of 47 mm were treated according to the method described under "laser ablation" above. Both 47 mm circles were then punched out of the 142 mm diameter disc. On the opposite side, two untreated 47 mm reference samples were punched out as shown in FIG. 14.

Tables 8 and 9 summarize the results of the comparison of four treated filter samples and four non-treated reference filter samples per membrane type. Shown are the performance results of single layer micro filtration membranes.

TABLE 8

Performance comparison membrane type 18357

| Trial | structure used | upstream area [cm$^2$] | total throughput [g] | benefit to ref. [%] |
| --- | --- | --- | --- | --- |
| 1 | Ref. sample | 13 | 98.70 | |
| 2 | Ref. sample | 13 | 100.80 | |
| 3 | Ref. sample | 13 | 91.60 | |
| 4 | Ref. sample | 13 | 86.00 | |
| | STDEV | 0 | 6.8 | |
| 1 | Ablation | 13 | 190.80 | 91.8 |
| 2 | Ablation | 13 | 183.10 | 84.1 |
| 3 | Ablation | 13 | 195.30 | 96.4 |
| 4 | Ablation | 13 | 187.10 | 88.3 |
| | STDEV | 0 | 5.2 | 5.2 |

TABLE 9

Performance comparison membrane type 15445 (prototype)

| Trial | structure used | upstream area [cm$^2$] | total throughput [g] | benefit to ref. [%] |
| --- | --- | --- | --- | --- |
| 1 | Ref. sample | 13 | 179.60 | |
| 2 | Ref. sample | 13 | 248.10 | |
| 3 | Ref. sample | 13 | 167.90 | |
| 4 | Ref. sample | 13 | 172.20 | |
| | STDEV | 0 | 37.7 | |
| 1 | Ablation | 13 | 456.50 | 154.2 |
| 2 | Ablation | 13 | 459.20 | 85.1 |
| 3 | Ablation | 13 | 486.30 | 189.6 |
| 4 | Ablation | 13 | 488.00 | 183.4 |
| | STDEV | 0 | 17.0 | 47.9 |

As can be seen from Tables 8 and 9, the laser-ablation treatment of the membranes to create macroscopic cavities extending from a first main surface of the membrane results in very high increases of the total throughput ranging between 84.1% and 189.6% benefit as compared to the non-treated membrane samples.

LIST OF REFERENCE NUMERALS

1 multi-level cavities;
2 first main surface (non-filtrate side) of the membrane;
3 micro-porous membrane (porous or micro-porous matrix with retentive layers);
4 filtrate side;
5 total thickness of the membrane;
6 diameter of a cavity;
7 penetration depth.

The invention claimed is:

1. A micro-porous filtration membrane, comprising a plurality of multi-level macroscopic discrete cavities extending from a first main surface of the membrane into the porous membrane which differ from the micropores constituting the micro-porous membrane and which are irregularly arranged within the membrane, wherein the penetration depth of the plurality of macroscopic cavities within the porous membrane is not uniform, the average penetration depth of the cavities into the membrane being from 30 to 80% of the total thickness of the membrane, wherein the individual diameter of the cavities measured at the opening of the membrane's first main surface is from 10 to 1000 µm, and wherein the diameter of the cavities is substantially the same throughout 50% of the penetration depth.

2. The micro-porous filtration membrane according to claim 1, wherein the shape of the plurality of cavities is a cylindrical, cone, or pyramidal shape.

3. The micro-porous filtration membrane according to claim 1, wherein the individual diameter of the cavities has a standard deviation of 20% or more from the arithmetic mean of the cavity diameter.

4. The micro-porous filtration membrane according to claim 1 having a surface porosity of from 15 to 50%.

5. The micro-porous filtration membrane according to claim 1, wherein the filter material is formed using a porous polymer membrane made from at least one of polyether sulfone, polyamide, a cellulose derivative, cellulose mixed ester, cellulose acetate, cellulose nitrate, cellulose, polypropylene, polyethylene, polytetrafluoroethylene, expanded polytetrafluoroethylene, polyvinylidene difluoride or polyvinyl chloride.

6. A method for producing a micro-porous filtration membrane according to claim 1, comprising the following steps:
   providing a micro-porous filtration membrane having a first and second main surface, and
   modifying the first main surface of the membrane so as to mechanically, chemically and/or thermally form a plurality of multi-level macroscopic discrete cavities extending from a first main surface of the membrane into the porous membrane.

7. The method according to claim 6, wherein the step of modifying the first main surface of the membrane is carried out by spiking using a plurality of sharp needles.

8. A method of using the micro-porous filtration membrane according to claim 1 in sterilizing processes in food and beverage filtration of water, wine, beer or biopharmaceutical filtration of cell and bacteria nutrition media or clarification and purification filtration of cell and bacteria broths.

9. A method for improving the throughput and/or flow rate of a micro-porous filtration membrane, comprising the step of modifying a first main surface of the membrane so as to mechanically, chemically and/or thermally form a plurality of multi-level macroscopic discrete cavities extending from a first main surface of the membrane into the porous membrane which differ from the micropores constituting the micro-porous membrane and which are irregularly arranged within the membrane, wherein the penetration depth of the plurality of macroscopic cavities within the porous membrane is not uniform, the average penetration depth of the cavities into the membrane being from 30 to 80% of the total thickness of the membrane, wherein the individual diameter of the cavities measured at the opening of the membrane's first surface is from 10 to 1000 and wherein the diameter of the cavities is substantially the same throughout 50% of the penetration depth.

* * * * *